US00PP20740P2

(12) United States Plant Patent
Belfield-Smith

(10) Patent No.: US PP20,740 P2
(45) Date of Patent: Feb. 9, 2010

(54) ***VIOLA* PLANT NAMED 'FLOVELLAVYEL'**

(50) Latin Name: *Viola×wiliamsii*
Varietal Denomination: Flovellavyel

(75) Inventor: Nick Belfield-Smith, Norwich (GB)

(73) Assignee: Floranova Ltd., Foxley, Dereham (GB)

( * ) Notice: Subject to any disclaimer, the term of this patent is extended or adjusted under 35 U.S.C. 154(b) by 0 days.

(21) Appl. No.: 12/290,133

(22) Filed: Oct. 28, 2008

(51) Int. Cl.
*A01H 5/00* (2006.01)

(52) U.S. Cl. ..... Plt./323

(58) Field of Classification Search ..... Plt./323
See application file for complete search history.

*Primary Examiner*—Susan B McCormick Ewoldt
(74) *Attorney, Agent, or Firm*—C. A. Whealy

(57) ABSTRACT

A new and distinct cultivar of *Viola* plant named 'Flovellavyel', characterized by its mounding and outwardly spreading plant habit; freely branching habit; early and freely flowering habit; long flowering period; and large pale violet and yellow-colored flowers.

1 Drawing Sheet

Botanical designation: *Viola×williamsii.*
Cultivar denomination: 'Flovellavyel'.

CROSS-REFERENCED TO RELATED APPLICATION

Title: *Viola* Plant Named 'Flovellempl'.
Applicant: Nick Belfield-Smith.
Filed concurrently with this application.

BACKGROUND OF THE INVENTION

The present invention relates to a new and distinct cultivar of *Viola*, botanically known as *Viola×williamsii* and hereinafter referred to by the name 'Flovellavyel'.

The new *Viola* plant is a product of a planned breeding program conducted by the Inventor in Foxley, Norfolk, United Kingdom. The objective of the breeding program was to create new outwardly spreading *Viola* cultivars with large flowers and attractive flower coloration.

The new *Viola* plant originated from a cross-pollination made by the Inventor in May, 2001, in Foxley, Norfolk, United Kingdom, of a proprietary selection of *Viola×williamsii* identified as code number USAHIL-2, not patented, as the female, or seed, parent with a proprietary selection of *Viola×williamsii* identified as code number USABVZ, not patented, as the male, or pollen, parent. The new *Viola* was discovered and selected by the Inventor as a single flowering plant from within the progeny of the stated cross-pollination in a controlled greenhouse environment in Foxley, Norfolk, United Kingdom in May, 2002.

Asexual reproduction of the new *Viola* plant by vegetative cuttings in a controlled greenhouse environment in Foxley, Norfolk, United Kingdom since September, 2002, has shown that the unique features of this new *Viola* plant are stable and reproduced true to type in successive generations.

SUMMARY OF THE INVENTION

Plants of the new *Viola* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Flovellavyel'. These characteristics in combination distinguish 'Flovellavyel' as a new and distinct cultivar of *Viola:*

1. Mounding and outwardly spreading plant habit.
2. Freely branching habit.
3. Early and freely flowering habit.
4. Long flowering period.
5. Large pale violet and yellow-colored flowers.

Compared to plants of the female parent selection, plants of the new *Viola* differ from plants of the female parent selection in the following characteristics:

1. Plants of the new *Viola* are not as open in plant habit as plants of the female parent selection.
2. Plants of the new *Viola* flower earlier than plants of the female parent selection.
3. Plants of the new Violet have larger flowers than plants of the female parent selection.
4. Plants of the new *Viola* and the female parent selection differ in flower color as plants of the female parent selection have blue-colored flowers.

Compared to plants of the male parent selection, plants of the new *Viola* differ from plants of the male parent selection in the following characteristics:

1. Plants of the new *Viola* are not as compact as plants of the male parent selection.
2. Plants of the new *Viola* are more outwardly spreading than and not as upright as plants of the male parent selection.
3. Plants of the new *Viola* have larger flowers than plants of the male parent selection.
4. Plants of the new *Viola* and the male parent selection differ in flower color as plants of the male parent selection have yellow-colored flowers.

Plants of the new *Viola* can be compared to plants of *Viola* 'Flovellempl', disclosed in a U.S. Plant patent application Ser. No. 12/290,132 filed concurrently. Plants of the new

*Viola* differ primarily from plants of 'Flovellempl' in flower color. In addition, plants of the new *Viola* have larger flowers than plants of 'Flovellempl'.

Plants of the new *Viola* can also be compared to plants of the *Viola×williamsii* 'Sunviobuho', disclosed in U.S. Plant Pat. No. 16,557. In side-by-side comparisons conducted in Foxley, Norfolk, United Kingdom, plants of the new *Viola* and 'Sunviobuho' differed in the following characteristics:

1. Plants of the new *Viola* were more mounding than plants of 'Sunviobuho'.
2. Plants of the new *Viola* had larger flowers than plants of 'Sunviobuho'.
3. Plants of the new *Viola* and 'Sunviobuho' differed in flower color.

BRIEF DESCRIPTION OF THE PHOTOGRAPHS

The accompanying colored photographs illustrate the overall appearance of the new *Viola*, showing the colors as true as it is reasonably possible to obtain in colored reproductions of this type. Colors in the photographs may differ slightly from the color values cited in the detailed botanical description which accurately describe the colors of the new *Viola*.

The photograph at the bottom of the sheet comprises a side perspective view of a typical flowering plant of 'Flovellavyel' grown in a container.

The photograph at the top of the sheet is a close-up view of typical flowers and leaves of 'Flovellavyel'.

DETAILED BOTANICAL DESCRIPTION

The aforementioned photographs and following observations, measurements and values describe plants grown in Encinitas, Calif. during the winter and under commercial practice in a polyethylene-covered greenhouse with day temperatures averaging 24° C., night temperatures averaging 16° C. and light levels averaging 4,000 foot-candles. Plants had been growing for 13 weeks when the photographs and description were taken. In the following description, color references are made to The Royal Horticultural Society Colour Chart, 2007 Edition, except where general terms of ordinary dictionary significance are used.

Botanical classification: *Viola×williamsii* 'Flovellavyel'.

Parentage:

*Female, or seed, parent*.—Proprietary selection of *Viola×williamsii* identified as code number USAHIL-2, not patented.

*Male, or pollen, parent*.—Proprietary selection of *Viola×williamsii* identified as code number USABVZ, not patented.

Propagation:

*Type*.—By vegetative cuttings.

*Time to initiate roots*.—About 18 to 26 days at 18° C. to 21° C.

*Time to produce a rooted young plant roots*.—About 35 to 45 days at 18° C. to 21° C.

*Root description*.—Fleshy; white in color.

*Rooting habit*.—Freely branching; moderately dense.

Plant description:

*Plant form/habit*.—Mounding and outwardly spreading plant habit; vigorous growth habit. Freely branching habit; about 18 lateral branches developing per plant; pinching is typically not required.

*Plant height*.—About 13 cm.

*Plant width* (*spread*).—About 36 cm.

*Lateral branches*.—Length: About 21 cm. Diameter: About 2 mm. Internode length: About 1.8 cm. Strength: Strong. Texture: Minute pubescence. Color: Close to 145A.

Foliage description:

*Arrangement*.—Alternate, simple.

*Length*.—About 4.6 cm.

*Width*.—About 2.4 cm.

*Shape*.—Ovate.

*Apex*.—Obtuse.

*Base*.—Rounded.

*Margin*.—Crenate.

*Texture, upper surface*.—Sparsely pubescent; slightly rough.

*Texture, lower surface*.—Smooth, glabrous.

*Venation pattern*.—Pinnate; arcuate.

*Color*.—Developing and fully expanded leaves, upper surface: Close to 137A; venation, close to 145A. Developing and fully expanded leaves, lower surface: Close to 146B; venation, close to 147C.

*Petiole*.—Length: About 3 cm. Diameter: About 1.5 mm. Texture, upper surface: Minute pubescence; scattered. Texture, lower surface: Minute pubescence. Color, upper surface: Close to 144A. Color, lower surface: Close to 146C.

Flower description:

*Flower type/habit*.—Single flowers borne in upper leaf axils; flowers face initially upright and then outwardly. Freely flowering habit with about 130 flowers and flower buds per plant.

*Fragrance*.—Faint; vanilla-like.

*Natural flowering season*.—Continuously flowering from spring through the summer in California. Flowers not persistent.

*Postproduction longevity*.—Flowers last about five days on the plant.

*Flower buds*.—Height: About 1.7 cm. Diameter: About 7 mm. Shape: Oblong. Color: Close to 1D.

*Flower diameter*.—About 4.4 cm by 3.5 cm.

*Flower depth*.—About 2 cm.

*Petals*.—Quantity per flower: Five in a single whorl; two upper petals, two lateral petals and one lower petal. Upper petals: Length: About 2.2 cm. Diameter: About 2.8 cm. Shape: Obovate with rounded apex and attenuate base; margin, entire. Texture, upper and lower surfaces: Smooth, glabrous; velvety. Color: Developing petals, upper surface: Close to 4D. Developing petals, lower surface: Close to 1D. Fully expanded petals, upper surface: Close to 83B. Fully expanded petals, lower surface: Slightly more grey than 90C. Lateral petals: Length: About 2.2 cm. Diameter: About 2 cm. Shape: Obovate with rounded apex and attenuate base; margin, entire. Texture, upper and lower surfaces: Smooth, glabrous; velvety. Color: Developing petals, upper surface: Close to 4D; venation towards the base, close to 83A. Developing petals, lower surface: Close to 1D. Fully expanded petals, upper surface: Close to 90B to 90D; venation towards base, close to 83A. Fully expanded petals, lower surface: Close to 8C tinted with close to 90C. Lower petal: Length: About 2.3 cm. Diameter: About 3.1 cm. Shape: Cordate with rounded and retuse apex and attenuate base; margin, entire. Texture, upper and lower surfaces: Smooth, glabrous; velvety. Color: Developing petals, upper surface: Close to 4D; venation towards the base, close to 83A. Developing petals, lower surface: Close to 1D. Fully expanded petals, upper surface: Close to 92A to 92B; venation towards base, close to 83A; central eye, close to 17A. Fully expanded petals, lower surface: Close to 8C tinted with close to 90D.

*Sepals*.—Quantity per flower: Typically five in a single whorl. Length: About 1.6 cm. Width: About 3.5 mm. Shape: Elliptic. Apex: Acute. Base: Obtuse. Margin: Entire. Texture, upper surface: Smooth, glabrous. Texture, lower surface: Minute pubescence. Color, upper and lower surfaces: Close to 147B.

*Peduncles*.—Length: About 7.4 cm. Diameter: About 2 mm. Texture: Minute pubescence; scattered. Color: Close to 138A.

*Reproductive organs*.—Stamens: Quantity per flower: Typically five. Filament length: Less than 1 mm. Filament color: Close to 145C. Anther shape: Elliptic, flat. Anther length: About 2 mm. Anther color: Close to 8D. Pollen amount: None. Pistils: Quantity per flower: One. Pistil length: About 6 mm. Stigma shape: Bulbous. Stigma color: Close to 145B. Style length: About 1 mm. Style color: Close to 145D. Ovary color: Close to 145D.

*Seed/fruit*.—Seed and fruit development have not been observed.

Disease/pest resistance: Plants of the new *Viola* have not been noted to be resistant to pathogens and pests common to *Viola*.

Garden performance: Plants of the new *Viola* have been observed to have good garden performance and to tolerate rain, wind and temperatures from about 0° C. to about 30° C.

It is claimed:

1. A new and distinct *Viola* plant named 'Flovellavyel' as illustrated and described.

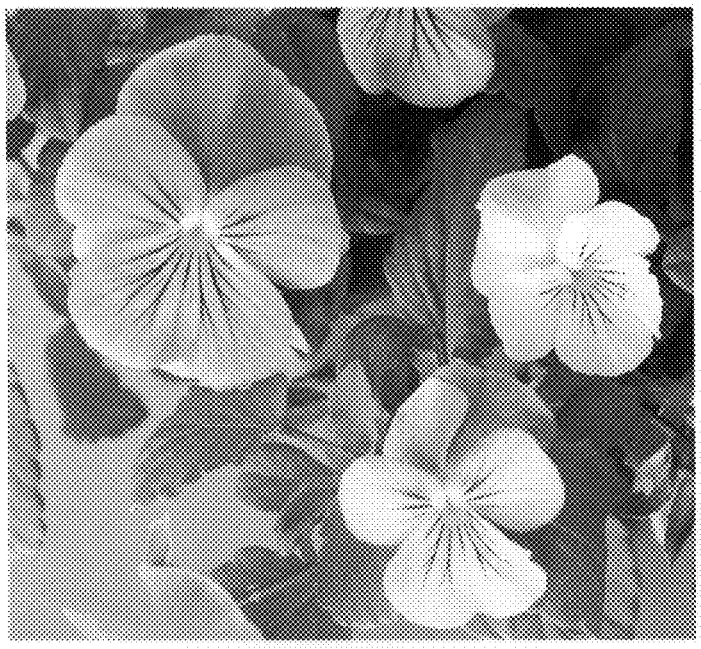
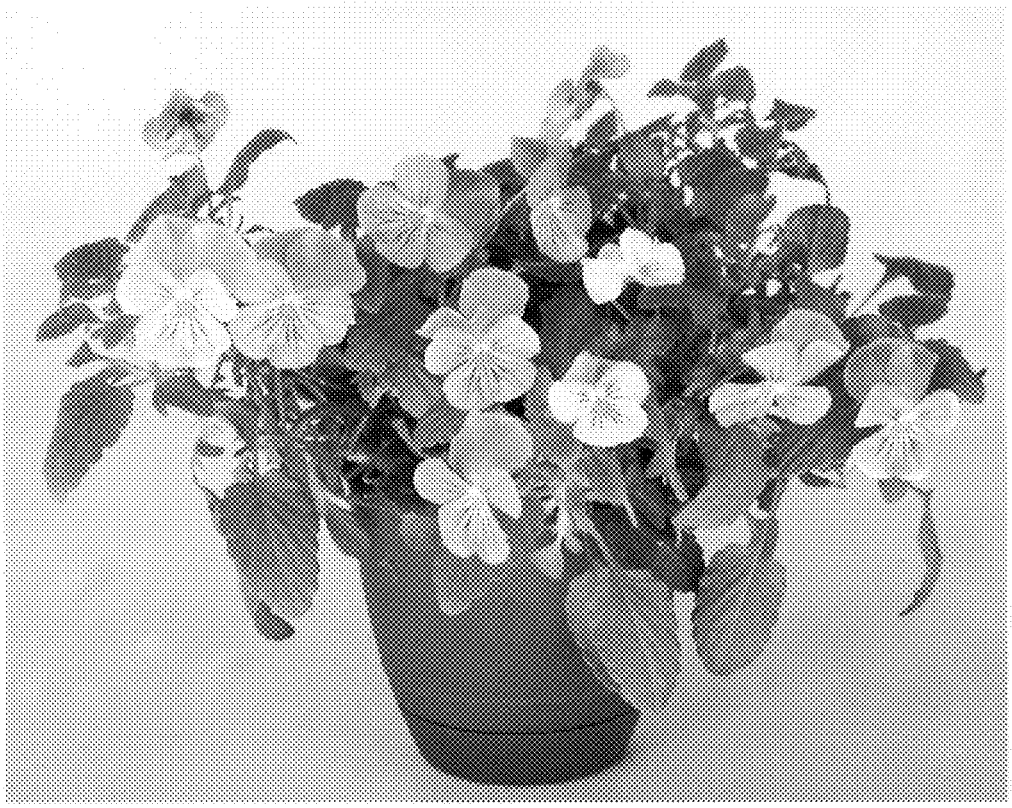

* * * * *